United States Patent
Li et al.

(10) Patent No.: US 11,098,285 B2
(45) Date of Patent: Aug. 24, 2021

(54) **VIRULENT *PSEUDOMONAS FLUORESCENS* PHAGE ΦPF1901, AND PHAGE ΦPF901 PREPARATION AND APPLICATION THEREOF**

(71) Applicant: Bohai University, Jinzhou (CN)

(72) Inventors: Jianrong Li, Jinzhou (CN); Defu Zhang, Jinzhou (CN); Qiuhua Zhu, Jinzhou (CN); Ming Zhang, Jinzhou (CN); Gang Song, Jinzhou (CN); Xuepeng Li, Jinzhou (CN); Xiangyang Yu, Jinzhou (CN); Peng Zhang, Jinzhou (CN); Qinghai Wang, Jinzhou (CN); Jian Zhang, Jinzhou (CN); Xudong Zhang, Jinzhou (CN); Jia Yao, Jinzhou (CN); Xiaohong Hu, Jinzhou (CN); Xuefei Liu, Jinzhou (CN); Fengling Bai, Jinzhou (CN); Tingting Li, Jinzhou (CN); Qiuying Li, Jinzhou (CN); Ying Bu, Jinzhou (CN); Shumin Yi, Jinzhou (CN); Tong Sun, Jinzhou (CN); Ying Liu, Jinzhou (CN); Tianhui Yan, Jinzhou (CN); Chun Chang, Jinzhou (CN)

(73) Assignee: Bohai University, Jinzhou (CN)

(*) Notice: Subject to any disclaimer, the term of this patent is extended or adjusted under 35 U.S.C. 154(b) by 0 days.

(21) Appl. No.: 16/596,249

(22) Filed: Oct. 8, 2019

(65) Prior Publication Data
US 2021/0024899 A1    Jan. 28, 2021

(30) Foreign Application Priority Data

Jul. 22, 2019  (CN) .......................... 201910660676.6

(51) Int. Cl.
*C12N 7/00* (2006.01)

(52) U.S. Cl.
CPC ...... *C12N 7/00* (2013.01); *C12N 2795/00021* (2013.01)

(58) Field of Classification Search
None
See application file for complete search history.

(56) References Cited

PUBLICATIONS

By Scanlon et al., The ISME Journal 2012 vol. 6, pp. 1148-1158 (Year: 2012).*

* cited by examiner

*Primary Examiner* — Shanon A. Foley
*Assistant Examiner* — Myron G Hill
(74) *Attorney, Agent, or Firm* — Troutman Pepper Hamilton Sanders LLP; Christopher C. Close, Jr.

(57) ABSTRACT

The present invention provides a virulent *Pseudomonas fluorescens* (*P. fluorescens*) phage ΦPf1901, and a phage ΦPf1901 preparation and an application thereof, and relates to the technical field of phage. The virulent *P. fluorescens* phage ΦPf1901 has an accession number of CCTCC M2019447. The virulent phage ΦPf1901 has a titer of $(1.4-3) \times 10^{10}$ PFU/mL. The virulent phage ΦPf1901 has an optimal multiplicity of infection (MOI) value of 0.0001. The virulent *P. fluorescens* phage ΦPf1901 provided by the present invention exhibits very high specificity and lytic ability to *P. fluorescens*, which can be used to control *P. fluorescens*, with strong lytic and scavenging effects on a host.

5 Claims, 4 Drawing Sheets

US 11,098,285 B2

VIRULENT PSEUDOMONAS FLUORESCENS PHAGE ΦPF1901, AND PHAGE ΦPF901 PREPARATION AND APPLICATION THEREOF

TECHNICAL FIELD

The present invention relates to the technical field of phage, and in particular to a virulent *Pseudomonas fluorescens* (*P. fluorescens*) phage ΦPf1901, and a phage ΦPf1901 preparation and an application thereof.

BACKGROUND

Aquatic products are favored by consumers because they feature high protein, low fat, and low calorie. With an increasing proportion of aquatic products in the dietary pattern of Chinese residents, they promote the rapid development of the aquaculture industry. According to the Food and Agriculture Organization (FAO) of the United Nations (UN), 29.2% of the total catch and farming quantity of aquatic products worldwide are used for marketing fresh, and their demands are growing by 10% every year. It follows that the popularity of aquatic products worldwide and their underlying economic value and potential are tremendous. However, differences in processing and packaging methods of aquatic products during storage may cause some microbes to get dominant gradually and produce bad odors and off-flavor metabolites, finally resulting in corruptive aquatic products, which not only lose nutritive value, but also cause harm to consumer's food safety and physical health. Among bacteria that cause corruption of fresh aquatic products, *Pseudomonas fluorescens* (*P. fluorescens*) is a dominant spoilage bacterium.

*P. fluorescens* is a dominant spoilage bacterium for both freshwater fish and seafood and also common in clinically contaminated blood and blood products. Provided that *P. fluorescens*-contaminated blood and blood products are transfused into a patient, there may be serious consequences, such as septicemia, septic shock, and intravascular coagulation. Because many existing antibiotics are insensitive to *P. fluorescens*, mortality will be high once such microbe is infected.

A principal method for controlling the growth of spoilage organisms in aquatic products is to use antibiotics, but their chronic massive use will bring such problems as environmental pollution, development of drug resistance, and food safety; moreover, because antibiotics feature long development period and high research and development costs, current research focuses on seeking for a new technology or product that can effectively control bacteria in aquatic products and functions in a completely harmless and eco-friendly manner, partially or completely replacing antibiotics. Phage control is attracting more and more attention due to a plurality of advantages, such as no pollution to the environment, no destruction of ecological environment, and no development of bacterial drug resistance.

Phage is a virus that specifically lyses bacteria, actinomycetes, and cyanobacteria, is mainly composed of proteins and nucleic acids, has no cell structure, and widely exists in soil, air, water, and organisms. There are two major types according to proliferation: virulent and temperate phages. Virulent phage refers to a bacteriophage which carries out replication and proliferation processes immediately following infection in a host bacterium and finally results in lysis of a host cell to release offspring phages, in which the proliferation process includes five steps: adsorption, entry, replication, assembly, and release. The virulent phage has been used to treat bacterial infections due to its strong lytic ability to a host bacterium. Development of phage preparations for drug-resistant bacterial infections has been a research focus in China and overseas.

So far, virulent *P. fluorescens* phages remain problems with respect to low titer and difficulty in application.

SUMMARY

In view of this, an objective of the present invention is to provide a virulent *Pseudomonas fluorescens* (*P. fluorescens*) phage ΦPf1901, and a phage ΦPf1901 preparation and an application thereof.

In order to achieve the foregoing invention objective, the present invention provides the following technical solutions:

A virulent *P. fluorescens* phage ΦPf1901 has an accession number of CCTCC M2019447.

Preferably, the virulent phage ΦPf1901 has a titer of $(1.4\text{-}3) \times 10^{10}$ PFU/mL.

Preferably, the virulent phage ΦPf1901 has an optimal multiplicity of infection (MOI) value of 0.0001.

The present invention provides an application of the virulent *P. fluorescens* phage ΦPf1901 in the inhibition of *P. fluorescens*.

Preferably, the quantity ratio of the virulent *P. fluorescens* phage ΦPf1901 to the *P. fluorescens* is (1-10):1.

The present invention further provides a preparation of the virulent *P. fluorescens* phage, where the content of the virulent phage therein is $(1.4\text{-}3) \times 10^{12}$ PFU.

Preferably, the content of the virulent phage therein is $1.42 \times 10^{12}$ PFU.

The present invention provides an application of the ΦPf1901 preparation in the inhibition of *P. fluorescens*.

Beneficial effects of the present invention: The virulent *P. fluorescens* phage ΦPf1901 provided by the present invention exhibits very high specificity and lytic ability to *P. fluorescens*, and has a titer of $(1.4\text{-}3) \times 10^{10}$ PFU/mL and an optimal multiplicity of infection (MOI) value of 0.0001; the preparation of the virulent *P. fluorescens* phage provided by the present invention has a virulent phage content of $(1.4\text{-}3) \times 10^{12}$ PFU, which can be used to control *P. fluorescens* in aquatic products, has strong lytic and scavenging effects on a host, and features strong environmental adaptability, wide tolerance ranges of pH and temperature, and insensitivity to chloroform.

DESCRIPTION OF BIOLOGICAL PRESERVATION

Figure 1:
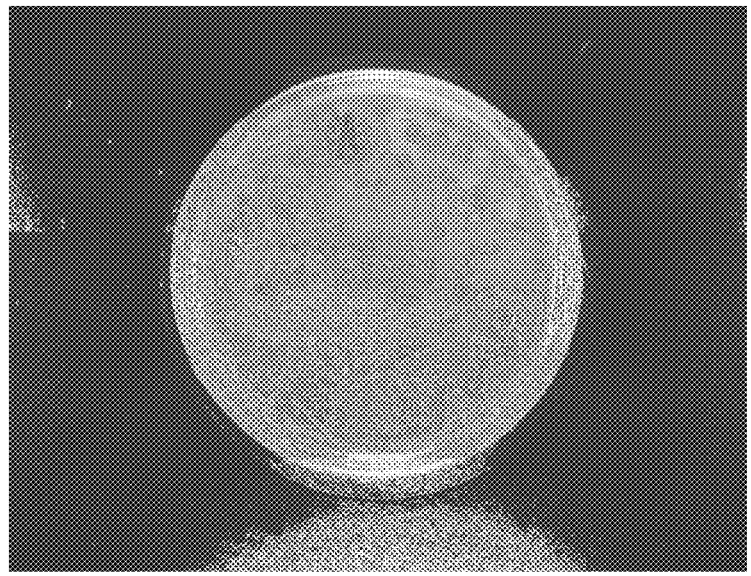
FIG. 1 shows a picture of plate lysis of lytic host cells of a virulent phage ΦPf1901 of the present invention.

The virulent *P. fluorescens* phage ΦPf1901 provided by the present invention is preserved in China Center for Type Culture Collection (CCTCC), Wuhan University, Bayi Road, Hongshan District, Wuhan City, Hubei Province on Jun. 26, 2019, with an accession number of CCTCC M2019447.

DETAILED DESCRIPTION

The present invention provides a virulent *Pseudomonas fluorescens* (*P. fluorescens*) phage ΦPf1901, with an accession number of CCTCC M2019447. The virulent *P. fluorescens* phage ΦPf1901 provided by the present invention is derived from a sewage sample. In a specific embodiment of the present invention, the virulent phage ΦPf1901 is derived from Jinzhou City, Liaoning Province; the virulent phage ΦPf1901 can specifically identify and lyse *P. fluorescens*. The titer of the virulent phage ΦPf1901 is preferably (1.4-3)×$10^{10}$ PFU/mL, and more preferably 1.42×$10^{10}$ PFU/mL; the virulent phage ΦPf1901 has an optimal multiplicity of infection (MOI) value of 0.0001.

In the present invention, the virulent phage ΦPf1901 is isolated and obtained by the following steps: 1) mixing a sewage sample with $CaCl_2$, conducting solid-liquid separation, collecting and filtering a liquid phase component, to obtain a filtrate; 2) mixing the filtrate obtained in step 1) with nutrient solution and *P. fluorescens* suspension, conducting shaking culture, to obtain a culture medium; and 3) centrifuging the culture medium, collecting supernatant, filtering, mixing and incubating the resulting filtrate with *P. fluorescens* suspension, mixing with the nutrient solution, growing in a plain agar plate to obtain the virulent phage ΦPf1901.

In the present invention, the solid-liquid separation is conducted after mixing the sewage sample with $CaCl_2$, and the filtrate is obtained by collecting and filtering the liquid phase component. In the present invention, the sewage sample preferably is derived from the wastewater discharged from Xiaoling River, Jinzhou City, Liaoning Province; in the present invention, the concentration of the $CaCl_2$ in the mixture is preferably 0.8-1.2 mmol/L, and more preferably 1.0 mmol/L; the role of the $CaCl_2$ is to cause phages in the sample to absorb host bacteria more easily. In the present invention, the solid-liquid separation is preferably centrifugation, the rotational speed of the centrifugation is preferably 8000 r/min, and the centrifugal time is preferably 10 min; in the present invention, the liquid phase component is collected and filtered after the solid-liquid separation, the filtering is preferably filtration by filter membrane, and the pore size of the filter membrane is preferably 0.22 μm.

In the present invention, the culture medium is obtained by mixing the filtrate with nutrient solution and *P. fluorescens* suspension and conducting shaking culture. In the present invention, the filtrate, the nutrient solution, and the *P. fluorescens* suspension are at a volume ratio of 20:5:2; the nutrient solution is preferably LB liquid medium; the *P. fluorescens* is preferably in logarithmic growth phase. In the present invention, the temperature of the shaking culture is preferably 30° C., the rotational speed of the shaking culture is preferably 130 r/min, and the time of the shaking culture is preferably 10-14 h, and more preferably 12 h.

In the present invention, after obtained the culture medium, the culture medium is centrifuged, followed by collecting and filtering the supernatant. In the present invention, the temperature of the centrifugation is preferably 4° C., the rotational speed of the centrifugation is preferably 8000 r/min, and the centrifugal time is preferably 10 min. In the present invention, the filtering is preferably filtration by filter membrane, and the pore size of the filter membrane is preferably 0.22 μm. In the present invention, after the filtering, the resulting filtrate is mixed and incubated with *P. fluorescens* suspension and then mixed with the nutrient solution, and is grown in a plain agar plate to obtain the virulent phage ΦPf1901. In the present invention, the volume ratio of the filtrate to the *P. fluorescens* suspension is preferably 1:2; the mixing and incubating time is preferably 10-20 min. In the present invention, the volume ratio of the filtrate to the nutrient solution is preferably 1:50; the nutrient solution is preferably LB medium with an agar content of 0.75 wt % at a temperature of 50° C. In the present invention, the plain agar plate is a plate that sterilized 1.5 wt % agar powder for 15 min at 121° C. In the present invention, a double-layer plate is formed after the foregoing procedure. In the present invention, the double-layer plate is incubated in a constant temperature incubator for 10-14 h at 30° C. after solidification; the double-layer plate requires no inverted culture, in which water favors phage adsorption.

After culturing and obtaining the virulent phage ΦPf1901, the present invention preferably further includes purification of the virulent phage. In the present invention, the purification includes the following steps: S1) selecting and mixing a single plaque on the foregoing double-layer plate well with SM buffer to obtain a phage suspension; S2) conducting the phage suspension on gradient dilution and then growing in the double-layer plate; and S3) repeating the foregoing S1) to S2) two to four times to obtain purified phages.

In the present invention, the single plaque is preferably mixed well with 1 mL of SM buffer, the mixing time is preferably greater than or equal to 4 h, and the mixing temperature is preferably 4° C.; the mixing is preferably conducted on a shaking table. In the present invention, the phage suspension prior to dilution is preferably oscillated; the dilution factor is preferably 10-fold gradient dilution, and more preferably selecting $10^{-5}$ and $10^{-6}$ diluents to grow on a double-layer plate. In the specific embodiment of the present invention, the diluent is preferably mixed with LB medium to prepare a double-layer plate after mixing with *P. fluorescens* suspension in logarithmic phase at a 2:1 volume ratio for 10-15 min. The foregoing double-layer plate purification steps are preferably to repeat three times to obtain purified phage ΦPf1901.

After obtaining the purified phage ΦPf1901, the present invention further includes storage of the purified phage ΦPf1901. In the present invention, the storage method is preferably to conduct the purified phage ΦPf1901 and SM buffer on mixing oscillation, centrifuge, collect supernatant, and store at 4° C.

The present invention further provides a preparation comprising the virulent *P. fluorescens* phage ΦPf1901, where the content of the virulent phage in the preparation is (1.4-3)×$10^{12}$ PFU, and preferably 1.42×$10^{12}$ PFU.

The present invention further provides applications of the virulent *P. fluorescens* phage and the preparation comprising the virulent *P. fluorescens* phage ΦPf1901 in the inhibition of *P. fluorescens*. In the present invention, the quantity ratio of the virulent *P. fluorescens* phage ΦPf1901 to the *P. fluorescens* is (1-10):1. In the present invention, the virulent *P. fluorescens* phage ΦPf1901 can be used to inhibit *P. fluorescens* in various environments, including but not limited to *P. fluorescens* in aquatic products.

The technical solutions of the present invention will be described in detail below in connection with Embodiments, but they should not be construed as the limitation of the protection scope of the present invention.

Embodiment 1

(1) Experimental Materials

Consumables: 0.22 μm and 0.45 μm filter membranes, Eppendorf tube (EP tube), test tubes, 50 mL centrifuge tubes, SM buffer, plain agar plate, LB plate, LB liquid medium, and LB semi-solid medium Host bacteria: *Pseudomonas fluorescens* (*P. fluorescens*)

Medium: LB liquid medium, and agar powder (2) Strain Culture

1) *P. fluorescens* was removed at −20° C. and cultured on a marked LB medium for 16-18 h at 30° C.

2) A single colony of *P. fluorescens* was picked up, grown on a LB liquid medium, and cultured for 8-10 h at 30° C. with shaking at 130 r/min until it became turbid.

(3) Isolation of Phage

1) Forty-five milliliters of sewage sample (wastewater at the outfall of Xiaoling River, Jinzhou City, Liaoning Province) was taken, $CaCl_2$ (which allowed phages in the sample to absorb host bacteria more easily) was added to a final concentration of 1 mmol/L, dissolved, mixed well, and centrifuged for 10 min at 8000 r/min for supernatant. After filtration through a filter membrane with a pore size of 0.22 μm, the resulting filtrate was stored at 4° C.

2) Twenty milliliters of the filtrate passed through the filter membrane was mixed with 5 mL of LB liquid medium and 2 mL of *P. fluorescens* suspension in logarithmic phase, and cultured on a shaking table overnight at 30° C. with shaking at 130 r/min.

3) After centrifugation for 10 min at 8000 r/min at 4° C. and filtration through a 0.22 μm filter membrane, 100 μl of supernatant was mixed with 200 μl of *P. fluorescens* suspension, and incubated for 15 min at room temperature, then mixed well with 5 mL of LB medium containing 0.75 wt % agar at 50° C., and poured onto a plain agar plate (1.5 wt % agar powder, sterilized for 15 min at 121° C.) to form a double-layer plate.

4) After solidification, the double-layer plate was placed in a constant temperature incubator, incubated overnight at 30° C., without inverted culture. Water favored phage adsorption.

(4) Purification of Phage (stored at 4° C. temporarily)

1) After culture overnight, a sterile inoculating needle was used to pick up a single clear plague from the foregoing plate with plagues into 1 mL of SM buffer and mixed well on a shaking table for 4 h at 4° C. (alternatively, placed overnight).

Figure 5:
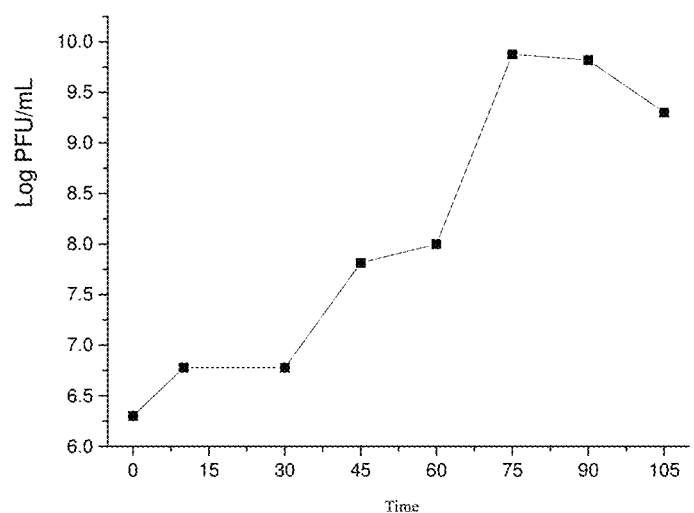
FIG. 5 shows a plot of one-step growth curve of the virulent phage ΦPf1901.
Figure 6:
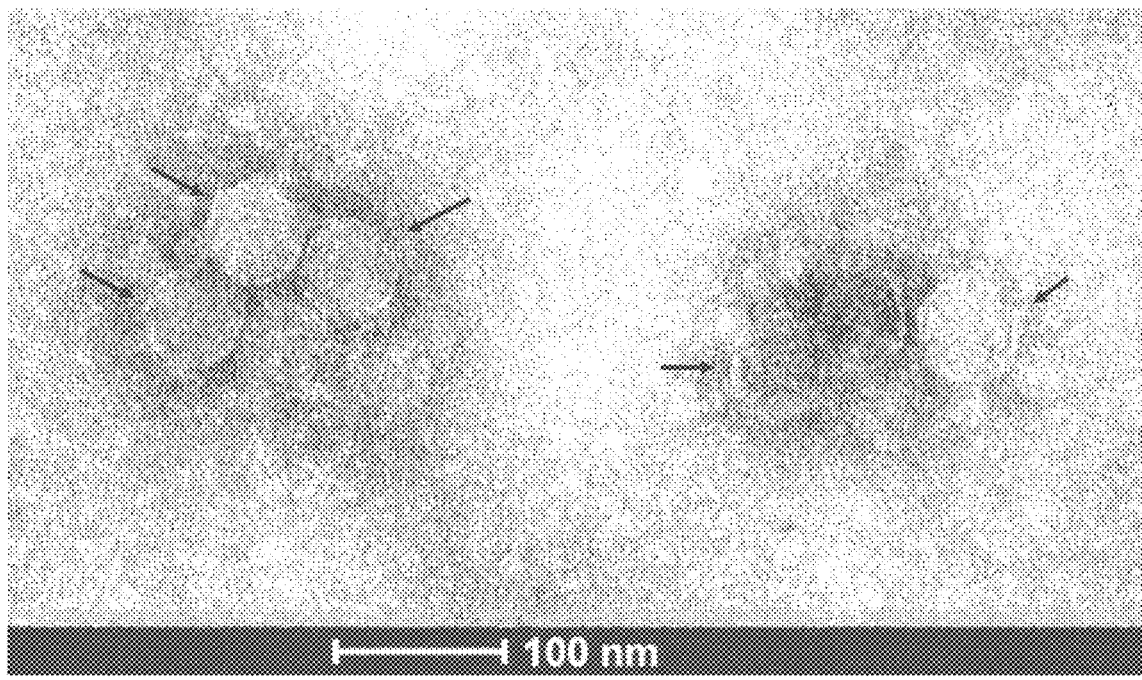
FIG. 6 shows a TEM graph of the virulent phage ΦPf1901.

2) After oscillating and mixing well on a vortex mixer, 10 μL of phage suspension was diluted gradiently (dilution factor was selected at $10^{-5}$ and $10^{-6}$). Then, 100 μL of *P. fluorescens* suspension in logarithmic phase was mixed with 200 μL of phage diluent for 15 min at room temperature, followed by preparing a double-layer plate with 5 mL of LB medium containing 0.75 wt % agar and incubating overnight at a constant temperature of 30° C. Pure phage ΦPf1901 was obtained after the double-layer plate method was repeated three times. The one-step growth curve of the phage ΦPf1901 is illustrated in FIG. 5 and its TEM graph is shown in FIG. 6.

(5) Phage Titration and Determination of Optimal Multiplicity of Infection (MOI)

A solid plain agar plate was prepared in advance as a bottom layer of a double-layer plate. Sterile SM buffer was used for 10-fold serial gradient dilution of phage proliferation liquid. Then, 100 μL of phage diluent with proper countable dilution factors ($10^{-7}$ and $10^{-8}$) and 200 μL of *P. fluorescens* suspension in logarithmic phase were added to 5 mL of LB semi-solid medium at 45-50° C., mixed well on a vortex mixer, and poured onto the bottom plate. After sufficient condensation, the medium was inverted and incubated at 30° C. in a constant temperature incubator until clear plagues appeared (for 12 h). For each dilution factor three parallel groups were set and averaged. The calculation formula of phage titer is as follows: phage titer (PFU/mL) =number of plagues×dilution factor×10. As shown in Table 1, the phage titer is calculated as $1.42 \times 10^{10}$ PFU/mL.

TABLE 1

Phage titration results

| Dilution factor | Number of plagues | Phage titer | Group average of phage titer | Overall average of phage titer |
|---|---|---|---|---|
| $10^7$ | 141 | $1.41 \times 10^{10}$ | $1.36 \times 10^{10}$ | $1.42 \times 10^{10}$ |
| $10^7$ | 120 | $1.20 \times 10^{10}$ | | |
| $10^7$ | 148 | $1.48 \times 10^{10}$ | | |
| $10^8$ | 5 | $5.00 \times 10^9$ | $1.47 \times 10^{10}$ | |
| $10^8$ | 22 | $2.20 \times 10^{10}$ | | |
| $10^8$ | 17 | $1.70 \times 10^{10}$ | | |

TABLE 2

Optimal MOIs of the virulent phage ΦPf1901

| Bacterial count | Phage count | Optimal MOI | Phage titer at 12 h |
|---|---|---|---|
| $2.236 \times 10^9$ | $10^{10}$ | 10 | $1.8 \times 10^{10}$ |
| $2.236 \times 10^9$ | $10^9$ | 1 | $6.3 \times 10^{11}$ |
| $2.236 \times 10^9$ | $10^8$ | 0.1 | $1.1 \times 10^{10}$ |
| $2.236 \times 10^9$ | $10^7$ | 0.01 | $1.0 \times 10^{10}$ |
| $2.236 \times 10^9$ | $10^6$ | 0.001 | $2.0 \times 10^{10}$ |
| $2.236 \times 10^9$ | $10^5$ | 0.0001 | $1.8 \times 10^{11}$ |

(6) Storage of Phage

Five milliliters of SM buffer were added onto the phage ΦPf1901 plate which had conducted pure culture three times (for a plate with a diameter of 9 cm, 5 mL of SM buffer was added; for a plate with a diameter of 15 cm, 10 mL of SM buffer was added), oscillating on a shaking table for hours at 4° C. The liquid on the plate was transferred into a sterile EP tube and centrifuged for 15 min at 5000 r/min at 4° C. to remove bacteria debris. The resulting supernatant was pipetted into a new EP tube and stored at 4° C. temporarily.

(7) Determination of Adsorption Rate

With MOI=0.1, phage ΦPf1901 with a titer of $10^{10}$ and *P. fluorescens* suspension with a bacteria concentration of $10^9$ were added to culture on a shaking table; 100 μL of mixture was pipetted for titration at different culture times; the test was repeated three times.

The calculation formula is: phage adsorption rate=(1− unabsorbed phage titer/initial phage titer)×100%.

Figure 4:
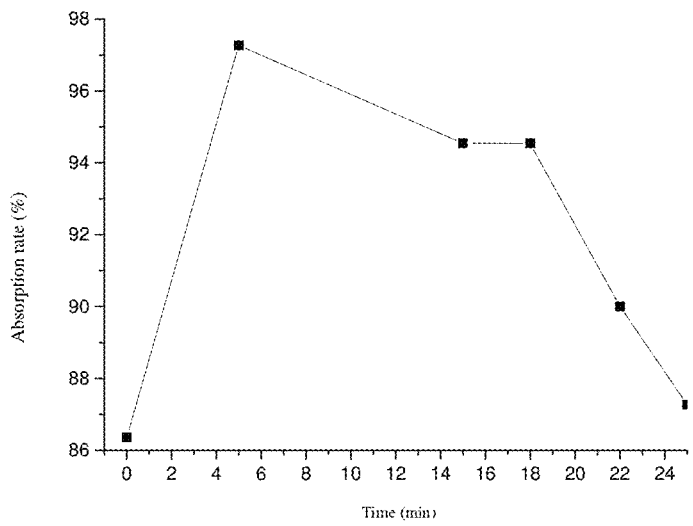
FIG. 4 shows the adsorption rate of the virulent phage ΦPf1901.

From FIG. 4, 86% of the phage ΦPf1901 absorbed immediately after the phage ΦPf1901 was mixed with the host bacteria suspension, 97% of the phage ΦPf1901 absorbed after incubation for 5 min, and the adsorption rate of the phage ΦPf1901 reached more than 90% between 5 min and 22 min, suggesting that the phage ΦPf1901 exhibited a good adsorption rate.

(8) Measurement of Sensitivity to Chloroform

One milliliter of purified *P. fluorescens* phage ΦPf1901 proliferation liquid was pipetted, mixed well with 1% chloroform solution while oscillating; after standing still for 30 min at room temperature for stratification, supernatant was pipetted for titration; changes in phage titer were compared before and after chloroform treatment, and data were recorded.

Phage ΦPf1901 proliferation liquid: liquid of solid plate proliferation.

Phage ΦPf1901 suspension: phage proliferation liquid treated by NaCl and PEG 8000.

The titers of the phage ΦPf1901 proliferation liquid before and after chloroform treatment were $1.3 \times 10^{11}$ and $1.2 \times 10^{11}$, respectively.

The titers of the phage ΦPf1901 suspension before and after chloroform treatment were $2.4 \times 10^{10}$ and $1.2 \times 10^{11}$, respectively.

The test results are shown particularly in Table 3.

TABLE 3

Sensitivity of virulent phage ΦPf1901 to chloroform

| Phage | Presence of chloroform | Phage titer | Sensitivity to chloroform |
|---|---|---|---|
| Phage proliferation liquid | Yes | $1.3 \times 10^{11}$ | Insensitive |
|  | No | $1.2 \times 10^{11}$ |  |
| Phage suspension | Yes | $2.4 \times 10^{10}$ | Insensitive |
|  | No | $1.2 \times 10^{11}$ |  |

(9) Determination of Optimal Temperature Range

Two hundred microliters each of phage ΦPf1901 was placed in water bath kettles at room temperature (25° C.) and preset at 30° C., 40° C., 50° C., 60° C., 70° C., and 80° C., respectively, and titrated 60 min after incubation.

Figure 2:
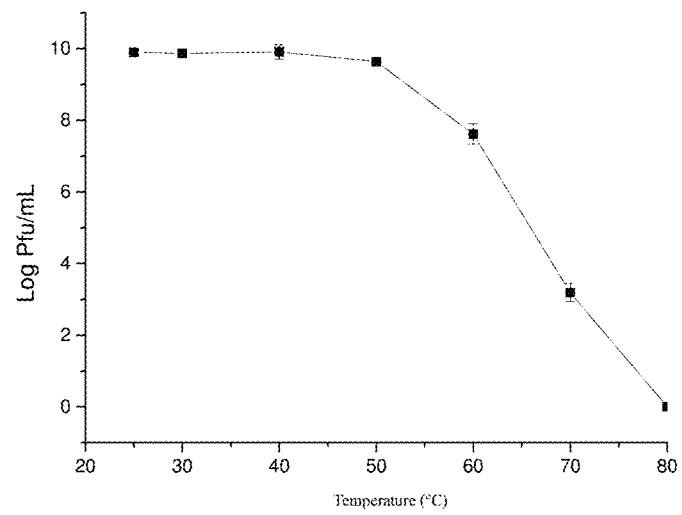
FIG. 2 shows the thermal stability of the virulent phage ΦPf1901.

Results are shown in FIG. 2. The phage ΦPf1901 could maintain high titers after treating when treating for 1 h at room temperature (25° C.), 30° C., 40° C., and 50° C.; at 60° C. and 70° C., the titer of the phage ΦPf1901 declined; at 80° C., the titer of the phage ΦPf1901 was 0.

(10) Determination of Optimal pH Range

Ten percent of phage ΦPf1901 was placed on LB liquid media at pH 4, pH 5, pH 6, pH 7, pH 8, pH 9, pH 10, pH 11, and pH 12, respectively, and titrated 1 h after treatment at room temperature.

Figure 3:
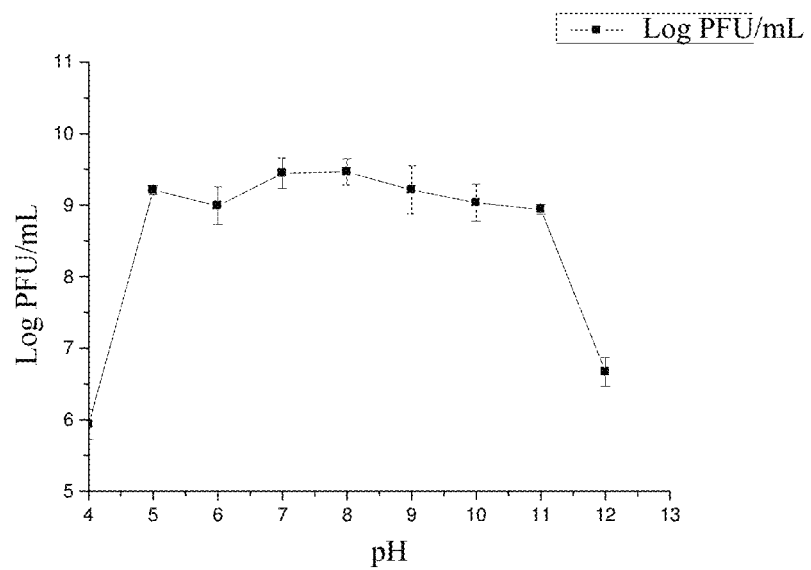
FIG. 3 shows the measurement of an optimum pH range of the virulent phage ΦPf1901.

Results are shown in FIG. 3. The phage ΦPf1901 could maintain high titers when treating for 1 h in LB liquid media at pH 5, pH 6, pH 7, pH 8, pH 9, pH 10, and pH 11; the titer of the phage ΦPf1901 was low at pH 4 and pH 12.

Embodiment 2

Detection of lytic ability of virulent phage ΦPf1901 to Pseudomonas fluorescens (P. fluorescens) (by plate method)

At room temperature, 200 μL of P. fluorescens suspension with a concentration of $10^9$ was mixed with 100 μL of phage ΦPf1901 diluent for 10-15 min and then with 5 mL of LB medium containing 0.75% agar to make a double-layer plate, which was cultured overnight at a constant temperature of 30° C. Result of plate lysis of lytic host cells is illustrated in FIG. 1. Through observation and measurement, plague was 1.36-3.06 mm in diameter.

Embodiment 3

Detection of lytic ability of virulent phage ΦPf1901 to Pseudomonas fluorescens (P. fluorescens) (by $OD_{600}$ method)

A single P. fluorescens was grown in 10 mL of LB broth and cultured on a shaking table overnight at 30° C. with shaking at 130 r/min, and then 200 μl of the purified phage ΦPf1901 was added to 5 mL of P. fluorescens suspension removed, while culturing on a shaking table for 2-4 h. Clarity was observed for the suspension every 30 min. Results are shown in Table 4.

TABLE 4

Lytic ability of virulent phage ΦPf1901 (by $OD_{600}$ method)

| Groups | Time/min |  |  |  |  |  |  |  |
|---|---|---|---|---|---|---|---|---|
|  | 0 | 30 | 60 | 90 | 120 | 150 | 180 | 210 |
| Control | 0.059 | 0.590 | 0.593 | 0.603 | 0.060 | 0.057 | 0.058 | 0.061 |
| Host bacteria | 0.301 | 0.280 | 0.273 | 0.257 | 0.252 | 0.214 | 0.215 | 0.177 |

Embodiment 4

Scavenging effect of virulent phage ΦPf1901 on Pseudomonas fluorescens (P. fluorescens) in tilapia fillets The ratio of virulent phage ΦPf1901 to P. fluorescens was set at 1:1 and 10:1, while a control group was assigned. An observation was made of the scavenging effect of phage on P. fluorescens in a tilapia fillet.

Detailed Steps:

Tilapias were purchased from a supermarket. The fish was filleted into split fillets weighed each 5±0.5 g using a sterile scalpel blade. The fillets were immersed in freshly prepared 70% alcohol and sterilized for 1 min, placed in a sterile plastic plate after sterilization, and air dried in a benchtop.

For the air-dried fillets, 0.1 ml of $10^4$ cfu/ml P. fluorescens suspension was spread evenly on one side. After inoculation, the fillets were placed in the benchtop for 15 min to allow the bacteria to absorb spontaneously.

Low concentration group: Fillets were spread evenly with 0.1 ml of $10^4$ PFU/ml phage ΦPf1901 suspension on the P. fluorescens inoculated surface;

High concentration group: Fillets were spread evenly with 0.1 ml of $10^5$ PFU/ml phage ΦPf1901 suspension on the P. fluorescens inoculated surface;

Control group: Fillets were spread evenly with 0.1 ml of 0.85% NaCl on the P. fluorescens inoculated surface;

Each fillet was stored in a sterile plate. Three parallel groups were set in each group, sealed with cling film, placed in an incubator at 25° C., and sampled at 0, 3, 6, 9, 12, 24, and 36 h, respectively. When sampling and testing, each fillet was removed and placed in a sterile sampling bag, in which 100 ml of 0.85% NaCl was added. After 10-fold gradient dilution on a solid LB plate and culture by the spread plate method, counting was carried out.

TABLE 5

Scavenging effect of virulent phage ΦPf1901 on *P. fluorescens* in tilapia fillets

| Group | Total plate count in a tilapia fillet at different sampling time (CFU/mL) | | | | | | |
|---|---|---|---|---|---|---|---|
| | 0 h | 3 h | 6 h | 9 h | 12 h | 24 h | 36 h |
| Control | 4.40E+04 Cf | 3.53E+04 Ad | 3.90E+04 Be | 3.10E+04 Ac | 9.90E+04 Ag | 1.83E+04 Ab | 1.50E+04 Aa |
| High concentration | 1.21E+04 Bab | 4.20E+03 Aa | 1.39E+04 Bde | 4.86E+04 Ag | 2.72E+04 Abc | 1.09E+04 Acd | 9.83E+04 ABef |
| Low concentration | 1.26E+03 Aa | 9.21E+02 Aa | 4.60E+03 Aa | 8.82E+03 Aa | 3.08E+04 Aa | 8.38E+04 Aa | 1.11E+05 Ba |

Figure 7:
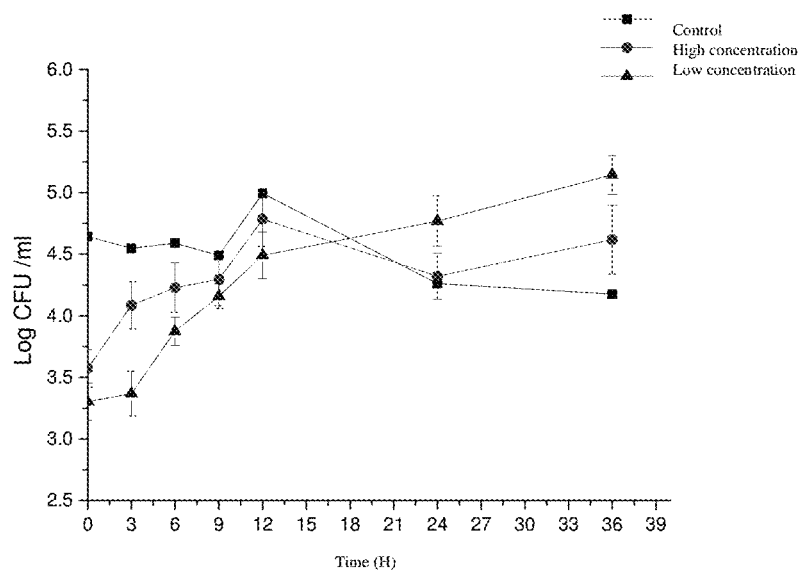
FIG. 7 shows the control effect of the virulent phage ΦPf1901 on *P. fluorescens* in tilapia fillets.

From Table 5 and FIG. 7, at 0-15 h, there was a significant control effect of high and low concentrations of phage ΦPf1901 suspension on *P. fluorescens*; at 15-36 h, the scavenging effect of the phage on the bacteria declined possibly because fillets were placed for a long time and water loss on the fillet surface resulted in low bacterial activity. By horizontal comparison among groups, low concentration group had a good control effect on *P. fluorescens* at 0-15 h. By vertical comparison among different groups, there was no significant difference between high and low concentration groups (p<0.05).

The foregoing descriptions are only preferred implementation manners of the present invention. It should be noted that for a person of ordinary skill in the art, several improvements and modifications may further be made without departing from the principle of the present invention. These improvements and modifications should also be deemed as falling within the protection scope of the present invention.

Deposit of Microorganisms:
Depository Institution: China Center for Type Culture Collection
Accession Number: CCTCCM2019447
Deposit Date: Jun. 11, 2019.

What is claimed is:

1. A method for inhibiting *P. fluorescens*, comprising the step of contacting *P. fluorescens* phage ΦPf1901 with a virulent *P. fluorescens* phage at a temperature of 20-50° C. and at a pH value of 5 to 11;
   wherein the virulent *P. fluorescens* phage ΦPf1901 is applied in a quantity ratio of the virulent *P. fluorescens* phage ΦPf1901 to the *P. fluorescens* of 0.0001-10:1 for 1 to 15 hours, and
   wherein the virulent *P. fluorescens* phage ΦPf1901 has an accession number of CCTCC M2019447.

2. The method according to claim 1, wherein the virulent *P. fluorescens* phage ΦPf1901 is applied in a quantity ratio of the virulent *P. fluorescens* phage ΦPf1901 to the *P. fluorescens* of 1-10:1.

3. The method according to claim 1, wherein the virulent *P. fluorescens* phage ΦPf1901 is applied in a quantity ratio of the virulent *P. fluorescens* phage ΦPf1901 to the *P. fluorescens* of 0.0001-10:1.

4. The method according to claim 1, wherein the content of the virulent *P. fluorescens* phage ΦPf1901 is $1.4 \times 10^{12}$ to $3 \times 10^{12}$ PFU.

5. The method according to claim 1, wherein the content of the virulent *P. fluorescens* phage ΦPf1901 is $1.42 \times 10^{12}$ PFU.

* * * * *